(12) United States Patent
Zhang (10) Patent No.: US 10,872,697 B2
(45) Date of Patent: Dec. 22, 2020

(54) TRIAGE DIALOGUE METHOD, DEVICE AND SYSTEM

(71) Applicant: BOE TECHNOLOGY GROUP CO., LTD., Beijing (CN)

(72) Inventor: Zhenzhong Zhang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 189 days.

(21) Appl. No.: 16/082,031

(22) PCT Filed: Jan. 10, 2018

(86) PCT No.: PCT/CN2018/072098
§ 371 (c)(1),
(2) Date: Sep. 4, 2018

(87) PCT Pub. No.: WO2019/000905
PCT Pub. Date: Jan. 3, 2019

(65) Prior Publication Data
US 2019/0385739 A1    Dec. 19, 2019

(30) Foreign Application Priority Data

Jun. 28, 2017    (CN) .......................... 2017 1 0507287

(51) Int. Cl.
*G16H 50/20*    (2018.01)
*G16H 40/67*    (2018.01)
*H04L 29/08*    (2006.01)

(52) U.S. Cl.
CPC ............. *G16H 50/20* (2018.01); *G16H 40/67* (2018.01); *H04L 67/10* (2013.01)

(58) Field of Classification Search
CPC ......... G16H 50/20; G16H 40/67; H04L 67/10
See application file for complete search history.

(56) References Cited

U.S. PATENT DOCUMENTS

2014/0019162 A1*  1/2014  Skowronski ........... G06Q 50/24
705/3

FOREIGN PATENT DOCUMENTS

WO    2016170368 A1    10/2016

OTHER PUBLICATIONS

Su, Pei-Hao, et al. "On-line active reward learning for policy optimisation in spoken dialogue systems." arXiv preprint arXiv: 1605.07669 (2016). (Year: 2016).*

(Continued)

*Primary Examiner* — Jialong He
(74) *Attorney, Agent, or Firm* — Dilworth & Barrese, LLP.; Michael J. Musella, Esq.

(57) ABSTRACT

A triage dialogue method, a device and a system are provided. The triage dialogue method includes: receiving triage dialogue content; dividing the triage dialogue content into a series of dialogue features, and generating dialogue feature vectors in one-to-one correspondence with the dialogue features; inputting the dialogue feature vectors into an encoder, and generating an intermediate representation vector through the encoder; determining whether the triage task is successfully completed according to the intermediate representation vector; and adjusting the triage dialogue policy according to the determination result of the triage task.

14 Claims, 3 Drawing Sheets

(56) References Cited

OTHER PUBLICATIONS

T. Nakano. "Generating Clinical Texts from Conversation", 2016, Neural Information Processing Systems(NIPS), Machine Learning for Health. (Year: 2016).*

Nallapati, Ramesh, et al. "Abstractive text summarization using sequence-to-sequence mns and beyond." arXiv preprint arXiv: 1602.06023 (2016). (Year: 2016).*

First Chinese Office Action from Chinese Application No. 201710507287.0 dated May 7, 2020.

Pei-Hao, Su et al., "On-Line Active Reward Learning for Policy Optimization in Spoken Dialogue Systems", Journal, Aug. 7-12, 2016, p. 2431-2441, issue 54, Proceedings of the 54th Annual Meeting of the Association for Computational Linguistics, Berlin Germany.

Engel et al., "Reinforcement Learning with Gaussian Process", Proceedings of ICML, 2005, Bonn, Germany.

* cited by examiner

TRIAGE DIALOGUE METHOD, DEVICE AND SYSTEM

The application claims priority to the Chinese patent application No. 201710507287.0, filed Jun. 28, 2017, the disclosure of which is incorporated herein by reference as part of the application.

TECHNICAL FIELD

Embodiments of the present invention relate to triage dialogue method, device and system.

BACKGROUND

Intelligent triage refers to the diagnosis of possible diseases based on the patient's main symptoms and signs, the determination of the priority of illness and its affiliated specialist, and the recommendation of effective visiting paths. Compared with the traditional outpatient triage, intelligent triage can determine the disease more quickly and more accurately and give reasonable advices. Therefore, under the current situation of tense social medical resources, intelligent triage is widely concerned by the medical community and has broad application prospect.

Particularly, the main task of the triage dialogue system is to quickly and accurately determine the affiliated specialist according to the patient's symptoms and signs, and give an effective visiting path. In order to finish this task, the intelligent triage system needs human-computer interaction with the patient to collect the patient's symptom and sign information. In general, the more times the intelligent triage system interacts with the patient, the more comprehensive the symptoms and the signs collected, and the more accurate the determination will be. However, the more times the intelligent triage system interacts with the patient also means more time it takes, which can delay the patient's visiting time and waste medical resources. Therefore, the key to the successful completion of the triage task by the intelligent triage system is the ability of accurately determining whether the task is successfully completed in the human-machine interaction process. The traditional triage system is usually based on a manually written rule base or based on a machine learning method (e.g., an Airdoc triage system). However, neither of the two methods explicitly evaluates whether the intelligent triage task is successfully completed.

SUMMARY

An embodiment of the disclosure provides a triage dialogue method, comprising: receiving triage dialogue content; dividing the triage dialogue content into a series of dialogue features, and generating dialogue feature vectors in one-to-one correspondence with the dialogue features; inputting the dialogue feature vectors into an encoder, and generating an intermediate representation vector through the encoder; determining whether a triage task is successfully completed according to the intermediate representation vector; and adjusting a triage dialogue policy according to a determination result of the triage task.

For example, the encoder adopts bidirectional gated recurrent unit (BGRU) network; and based on a forward hidden sequence and a backward hidden sequence of the BGRU network, the intermediate representation vector h is:

$$h = \frac{1}{T}\sum_{i=1}^{T} m_i,$$

in which $m_i = [\vec{M}_i; \overline{m}_i]$ represents a concatenation between the $i^{st}$ element $\vec{m}_i$ in the forward hidden sequence $\vec{M}_{1:T}$ and the $i^{st}$ element $\overline{m}$ in the backward hidden sequence $\overline{m}_{T:1}$; and T represents the number of the dialogue features.

For example, determining whether the triage task is successfully completed according to the intermediate representation vector includes: calculating success probability of the completion of the triage task based on previous intermediate representation vectors and the intermediate representation vector.

For example, determining whether the triage task is successfully completed is characterized as Gaussian process; and the success probability is:

$$p(y = 1 \mid h, H) = \phi\left(\frac{\mu_*}{\sqrt{1 + \sigma_*^2}}\right),$$

in which H represents the previous intermediate representation vectors; h represents the intermediate representation vector and is the current intermediate representation; $y \in \{-1, 1\}$, and y=1 represents the successful completion of the triage task; $\varphi(\bullet)$ represents the distribution function of standard normal distribution; $\mu_*$ and $\sigma_*^2$ respectively represent a posterior mean and a posterior variance of $f(h)$; and $f(\bullet)$ represents a potential function which is characterized as the Gaussian process.

For example, when the success probability falls into a failure interval, the determination result is that the triage task is determined to have failed; when the success probability falls into an uncertainty interval, the determination result is that whether the triage task is successfully completed is uncertain; or when the success probability falls into a success interval, the determination result is that the triage task is determined to have been completed.

For example, adjusting the triage dialogue policy according to the determination result of the triage task includes: continuing to interact with the user when the determination result is that the triage task is determined to have failed; prompting the user to provide feedback information and determining whether to continue to interact with the user according to the feedback information when the determination result is that whether the triage task is successfully completed is uncertain; or ending the dialogue with the user when the determination result is that the triage task is determined to have been completed.

For example, determining whether to continue to interact with the user according to the feedback information when the determination result is that whether the triage task is successfully completed is uncertain includes: ending the dialogue with the user when the feedback information indicates that the triage task has been completed; or selecting information with the greatest information gain to interact with the user when the feedback information indicates that the triage task has not been completed.

For example, selecting the information with the greatest information gain to interact with the user includes: calculating information gains of different symptoms, and determining the symptom relevant to the greatest information gain; and selecting the symptom relevant to the greatest information gain to interact with the user.

An embodiment of the disclosure provides a triage dialogue device, comprising a processor and a memory, wherein the memory is configured to store instructions; and the following operations are implemented when the instructions are executed by the processor: receiving triage dialogue content; dividing the triage dialogue content into a series of dialogue features, and generating dialogue feature vectors in one-to-one correspondence with the dialogue features; inputting the dialogue feature vectors into an encoder, and generating an intermediate representation vector through the encoder; determining whether a triage task is successfully completed according to the intermediate representation vector; and adjusting a triage dialogue policy according to a determination result of the triage task.

For example, the encoder adopts BGRU network; and based on a forward hidden sequence and a backward hidden sequence of the BGRU network, the intermediate representation vector h is:

$$h = \frac{1}{T}\sum_{i=1}^{T} m_i,$$

in which $m_i = [\vec{m}_i; \overline{m}_i]$ represents a concatenation between the $i^{st}$ element $\vec{m}_i$ in the forward hidden sequence $\vec{m}_{1:T}$ and the $i^{st}$ element $\overline{m}$ in the backward hidden sequence $\overline{m}_{T:1}$; and T represents the number of the dialogue features.

For example, determining whether the triage task is successfully completed according to the intermediate representation vector includes: calculating success probability of the completion of the triage task based on the previous intermediate representation vectors and the intermediate representation vector.

For example, determining whether the triage task is successfully completed is characterized as Gaussian process; and the success probability is:

$$p(y = 1 \mid h, H) = \phi\left(\frac{\mu_*}{\sqrt{1 + \sigma_*^2}}\right),$$

in which H represents the previous intermediate representation vectors; h represents the intermediate representation vector and is the current intermediate representation; $y \in \{-1, 1\}$, and y=1 represents the successful completion of the triage task; $\varphi(\bullet)$ represents the distribution function of standard normal distribution; $\mu_*$ and $\sigma_*^2$ respectively represent the posterior mean and the posterior variance of $f(h)$; and $f(\bullet)$ represents the potential function which is characterized as the Gaussian process.

For example, when the success probability falls into a failure interval, the determination result is that the triage task is determined to have failed; when the success probability falls into an uncertainty interval, the determination result is that whether the triage task is successfully completed is uncertain; or when the success probability falls into a success interval, the determination result is that the triage task is determined to have been completed.

For example, adjusting the triage dialogue policy according to the determination result of the triage task includes: continuing to interact with the user when the determination result is that the triage task is determined to have failed; prompting the user to provide feedback information and determining whether to continue to interact with the user according to the feedback information when the determination result is that whether the triage task is successfully completed is uncertain; or ending the dialogue with the user when the determination result is that the triage task is determined to have been completed.

For example, determining whether to continue to interact with the user according to the feedback information when the determination result is that whether the triage task is successfully completed is uncertain includes: ending the dialogue with the user when the feedback information indicates that the triage task has been completed; or selecting information with the greatest information gain to interact with the user when the feedback information indicates that the triage task has not been completed.

For example, selecting the information with the greatest information gain to interact with the user includes: calculating information gains of different symptoms, and determining the symptom relevant to the greatest information gain; and selecting the symptom relevant to the greatest information gain to interact with the user.

For example, the triage dialogue device further comprises an interactive interface, wherein the interactive interface is configured to interact with the user.

An embodiment of the disclosure provides a computer-readable storage medium, wherein computer instructions are stored on the computer readable storage medium; and the following operations are implemented when the computer instructions are executed by a processor: receiving triage dialogue content; dividing the triage dialogue content into a series of dialogue features, and generating dialogue feature vectors in one-to-one correspondence with the dialogue features; inputting the dialogue feature vectors into an encoder, and generating an intermediate representation vector through the encoder; determining whether a triage task is successfully completed according to the intermediate representation vector; and adjusting a triage dialogue policy according to a determination result of the triage task.

BRIEF DESCRIPTION OF THE DRAWINGS

Simple description will be given below to the accompanying drawings required to be used in the description of the embodiments to provide a more clear understanding of the technical proposals in the embodiments of the present invention. Obviously, the drawings described below only involve some embodiments of the present invention but are not intended to limit the present invention. Other accompanying drawings may also be obtained by those skilled in the art without creative efforts on the basis of these accompanying drawings.

DETAILED DESCRIPTION

For more clear understanding of the objectives, the technical proposals and the advantages of the present invention, more detailed description will be given below to the present invention with reference to the embodiments. Obviously, the preferred embodiments are only partial embodiments of the present invention but not all the embodiments. All the other embodiments obtained by those skilled in the art without creative efforts on the basis of the embodiments of the present invention shall fall within the scope of protection of the present invention.

Embodiments of the present invention provide triage dialogue device, method and system based on active reward learning, which can rapidly and accurately determine the affiliated specialist according to symptoms and signs of users (e.g., patients) and give effective visiting advices. During each round of triage dialogue, the embodiment explicitly determines whether the triage task can be successfully completed, and adjusts the dialogue policy according to the determination result. For instance, a reward model is built by using the active learning method of the Gaussian process, and the triage dialogue policy is adjusted according to an enhanced signal outputted from the reward model to maximize the expected reward value (i.e., to complete the triage task quickly and accurately). The triage dialogue device, method and system have, but not limited to, the following advantages: (1) determining whether user feedback is needed by adoption of active learning method, so as to reduce the burden on the users; (2) being favorable for reducing the influence of noise data on dialogue policy learning, and improving the performances; and (3) learning the dialogue policy through the explicit feedback of the users, and being favorable for rapidly and accurately completing the triage task.

For instance, when the user (e.g., the patient) interacts with the triage dialogue system, the triage dialogue device, method and system provided by the embodiment of the present invention can complete the triage dialogue as shown in Table 1 below together with the user.

TABLE 1

|  | Triage dialogue device (for instance, voice output or display output): do you need any help? |
|---|---|
| Human-machine Dialogue 1 | User (for instance, voice input or input through a touch panel): the right hand is bitten by a snake. Triage dialogue device: can you describe the symptoms? |
| Human-machine Dialogue 2 | User: redness and pain of the right hand, palpitation, chest tightness. Triage dialogue device: can you describe the type, color or shape of the snake? |
| Human-machine Dialogue 3 | User: short and thick body, very short tail, darkish brown. Triage dialogue device: it is recommended to register the emergency department and timely inject purified crotalus antivenin. |

In the above example, the triage dialogue device learns that the injury is snake bite by interacting with the user, but at this point, the triage dialogue device is still not sure that whether it is toxic snake bit or non-toxic snake bit (the two kinds of snake bit have different processing methods). Therefore, the triage dialogue device continues to interact with the user, concludes from the symptoms that it is toxic snake bit, but is still not certain that which kind of snake bit it is (e.g., hemolytic toxin, neurotoxin or mixed toxin; different toxins correspond to different serums). The triage dialogue device determines that the user may be bitten by *Agkistrodon halys* from the shape of the snake by further interacting with the user, and finally suggests the user to register the emergency department and recommends treatment recommendations, and at this point, the triage task is successfully completed.

Detailed description will be given below to the triage dialogue device, method and system provided by the embodiment of the present invention with reference to the accompanying drawings.

Figure 1:
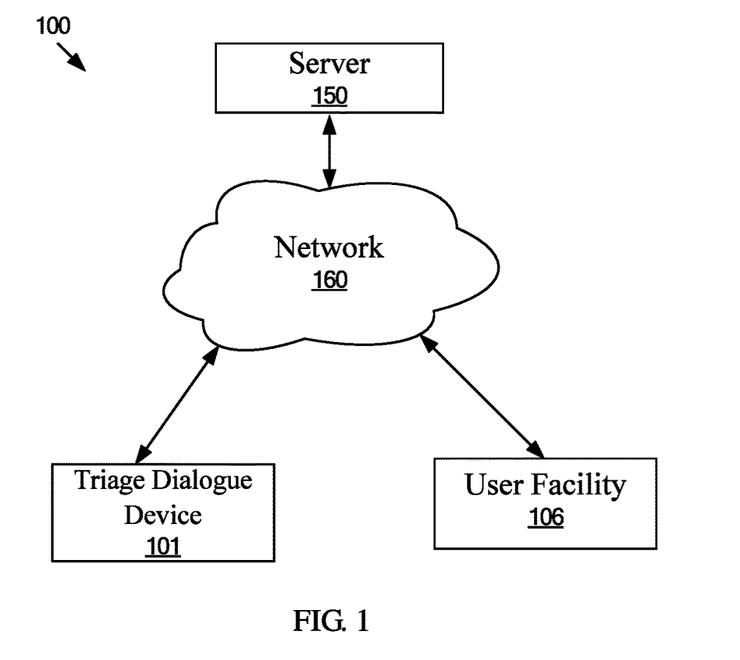
FIG. 1 is a schematic block diagram of a triage dialogue system provided by an embodiment of the present invention.

FIG. 1 is a schematic block diagram of a triage dialogue system 100 provided by the embodiment of the present invention. As illustrated in FIG. 1, the triage dialogue system 100 may comprise a triage dialogue device 101, a user facility 106, a server 150, etc. The devices and/or servers in the system 100 may be connected with each other via network 160. The devices and/or servers in the system 100 may be directly or indirectly communicated with each other. For instance, the devices and/or servers in the system 100 may send and receive data and/or signals to each other over the network 160.

The network 160 may include wireless network, wired network, and/or any combination of the wireless network and the wired network. For instance, the network 160 may include the local area network (LAN), the Internet, the Internet of Things based on the Internet and/or the telecommunication network, and/or any combination of the above networks. For instance, the network 160 may be medical network. The type and the function of the network 160 are not limited here in the present invention.

The server 150 may be a computing device including a processor and a memory. For instance, the server 150 may be a server or a cloud server in the LAN.

The triage dialogue device 101 may be a device for completing the triage task. Detailed description will be given below to the triage dialogue device 101 with reference to FIGS. 2A-5.

The user facility 106 may be a computing device including a processor and a memory. For instance, the user facility 106 may be a TV, a smart home appliance, a desktop computer, a notebook computer, a smart phone, a tablet PC, a game controller, a music player (e.g., an mp3 player) or other terminals including a processor and a memory (e.g., a mobile terminal or an intelligent terminal). In some embodiments, the user facility 106 may include a processor, a memory and other components such as an input unit and an output unit. In some examples, the user may interact with the triage dialogue device 101 through the user facility 106. For instance, the user may complete the dialogue with the triage dialogue device 101 by using an application (app) in the user facility 106.

In some embodiments, the device and/or the server in the system 100 may also include a display device (e.g., a liquid crystal display (LCD) or an organic light-emitting diode (OLED) display), an input device (e.g., a touch device, a keyboard, a microphone or a mouse), a loudspeaker, etc. No limitation will be given here in the present invention.

Figure 2A:
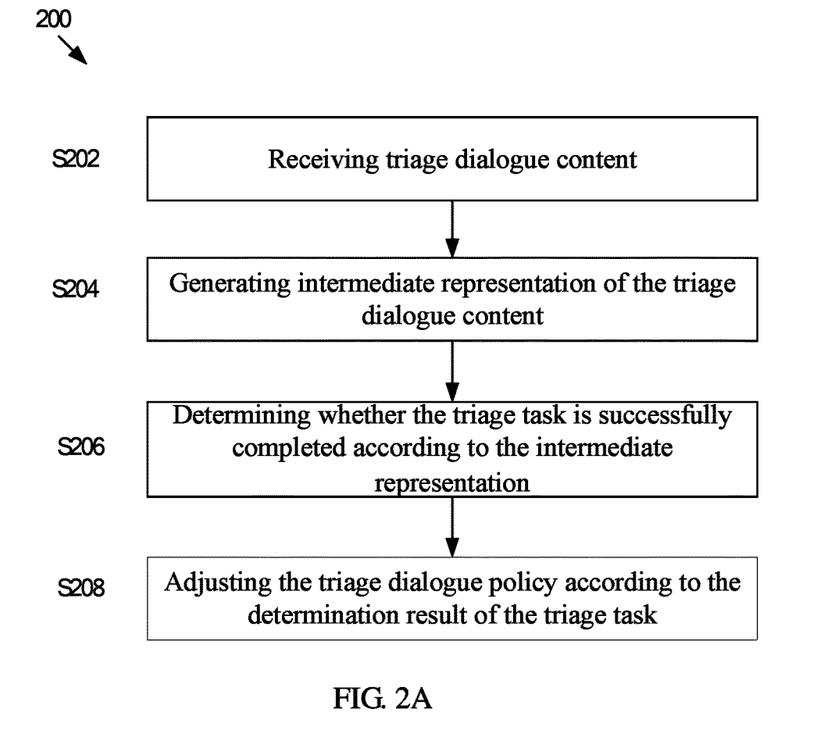
FIG. 2A is a first flowchart of a triage dialogue method provided by an embodiment of the present invention.

FIG. 2A is a first flowchart of a triage dialogue method 200 based on active reward learning, provided by the embodiment of the present invention. The triage dialogue method 200 comprises: S202: receiving triage dialogue content; S204: generating intermediate representation of the triage dialogue content; S206: determining whether the triage task is successfully completed according to the intermediate representation; and S208: adjusting the triage dialogue policy according to the determination result of the triage task.

Figure 2B:
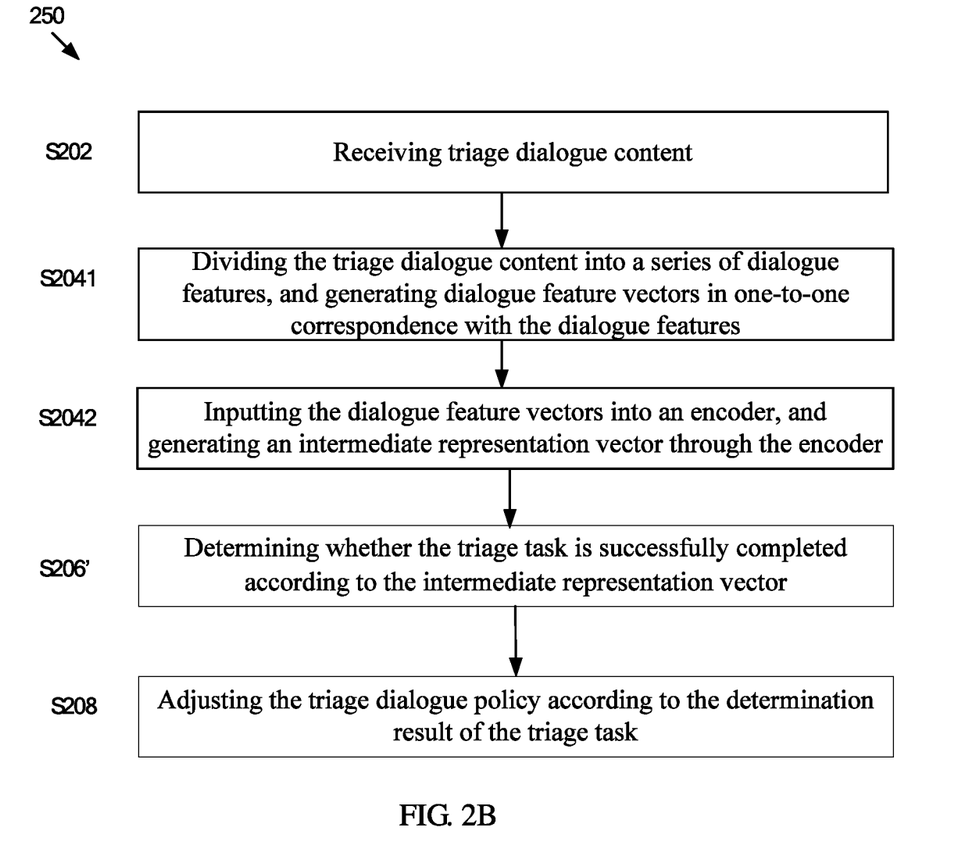
FIG. 2B is a second flowchart of a triage dialogue method provided by an embodiment of the present invention.

FIG. 2B is a second flowchart of a triage dialogue method 250 based on active reward learning, provided by the embodiment of the present invention. The triage dialogue method 250 comprises: S202: receiving triage dialogue content; S2041: dividing the triage dialogue content into a series of dialogue features, and generating dialogue feature vectors in one-to-one correspondence with the dialogue features; S2042: inputting the dialogue feature vectors into an encoder, and generating an intermediate representation vector through the encoder; S206': determining whether the triage task is successfully completed according to the intermediate representation vector; and S208: adjusting the triage dialogue policy according to the determination result of the triage task.

The method 200 in FIG. 2A and the method 250 in FIG. 2B are similar, and the differences include: the step S204 in FIG. 2A is exploded into the steps S2041 and S2042 in FIG. 2B; and the step S206 in FIG. 2A is replaced by the step S206' in FIG. 2B. When "intermediate representation" in the step S206 of FIG. 2A is "intermediate representation vector", the step S206 in FIG. 2A is the same with the step S206' in FIG. 2B.

The process of receiving the triage dialogue content in the step S202 includes: receiving the dialogue content that the triage dialogue device 101 interacts with the user. For instance, the above Table 1 shows three groups of dialogues (human-machine dialogue 1, human-machine dialogue 2 and human-machine dialogue 3) between the triage dialogue device 101 and the user. The user may interact with the triage dialogue device 101 through voice, a display (e.g., a touch panel with touch function), a somatosensory device, a keyboard, a mouse, an app of the user facility, etc.

In some embodiments, the intermediate representation is an intermediate representation vector h with fixed dimension dim(h). The process of generating the intermediate representation of the triage dialogue content in the step S204 of FIG. 2A at first includes: dividing the triage dialogue content into a series of dialogue features, and generating dialogue feature vectors in one-to-one correspondence with the triage features (the step S2041 in FIG. 2B).

Specifically, the triage dialogue content is divided into a series of dialogue features $\{d_1, d_2, \ldots, d_T\}$, in which each feature $d_i$ contains a group of human-machine dialogue, and $1 \leq i \leq T$. For instance, in combination with the above Table 1, the dialogue feature $d_1=\{$the right hand is bitten by a snake; can you describe the symptoms?$\}$; the dialogue feature $d_2=\{$redness and pain of the right hand, palpitation, chest tightness; can you describe the type, color or shape of the snake?$\}$; and the dialogue feature $d_3=\{$short and thick body, very short tail, darkish brown; it is recommended to register the emergency department and timely inject purified crotalus antivenin$\}$. The rest may be deduced by analogy.

Since the use of a computer to process natural language requires the conversion of the natural language into symbols that the machine can recognize, the dialog features can be digitized (namely the dialogue features $\{d_1, d_2, \ldots, d_T\}$ are converted into dialogue feature vectors $\{\vec{d}_1, \vec{d}_2, \ldots, \vec{d}_T\}$). For instance, the dialogue features can be digitized by utilization of word representation (namely using a real vector of specified length to represent a word). Moreover, for instance, words can be trained through neural network or deep learning to output vectors with specified dimensions, and the vector may be taken as the representation of the input word (e.g., word2vec). No limitation will be given to the method of digitizing the dialogue features in the present invention.

The process of generating the intermediate representation of the triage dialogue content in the step S204 of FIG. 2A further includes: building an encoder and a decoder; and inputting the dialogue feature vectors $\{\vec{d}_1, \vec{d}_2, \ldots, \vec{d}_{T-1}, \vec{d}_T\}$ into the encoder, and generating and outputting the intermediate representation vector h through the encoder (the step S2042 in FIG. 2B). One example of the encoder and the decoder is as shown in FIG. 5.

Figure 5:
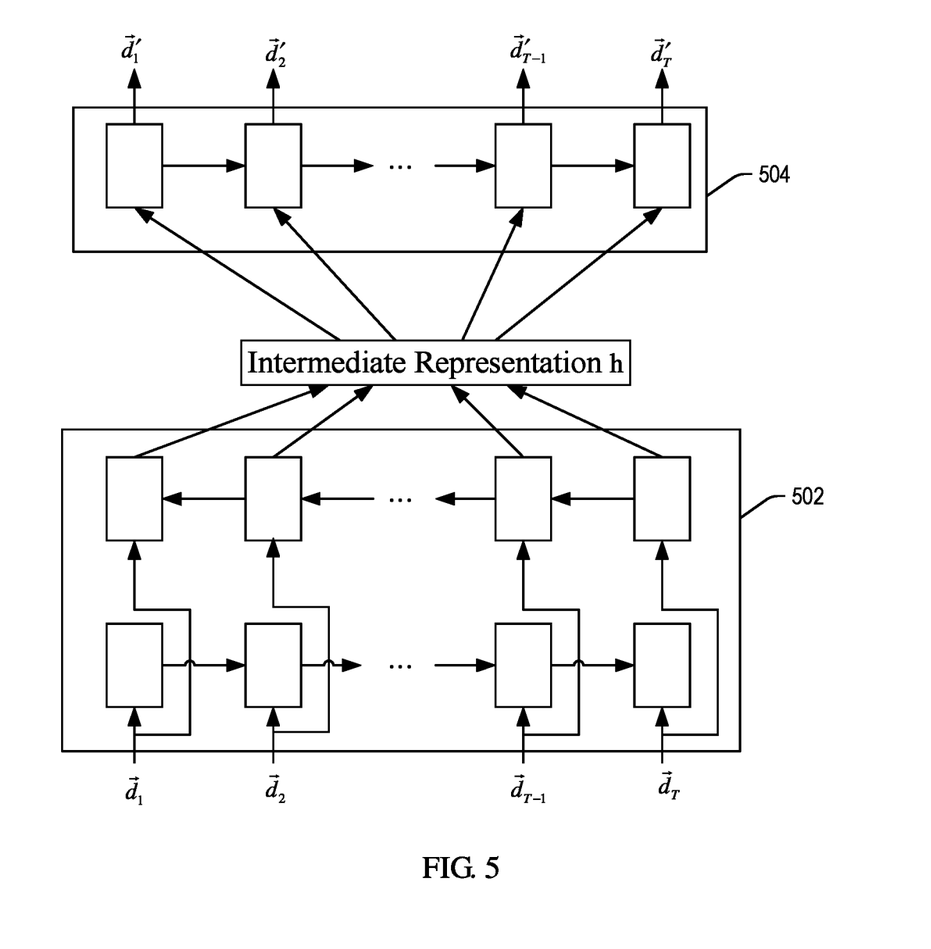
FIG. 5 is a schematic diagram of an encoder and a decoder in the embodiment of the present invention.

For instance, as shown in FIG. 5, an encoder 502 may adopt a bi-directional gated recurrent unit (BGRU) network. The BGRU network is a recurrent neural network (RNN) capable of alleviating the gradient dispersion problem. The BGRU encoder 502 calculates information of feature sequences in different directions (from forward to backward and from backward to forward) by the input of the dialogue feature vectors $\{\vec{d}_1, \vec{d}_2, \ldots, \vec{d}_T\}$. For instance, the $i^{st}$ element $\vec{m}$ in the forward hidden sequence $\vec{m}_{1:T}$ and the $i^{st}$ element $\overleftarrow{m}$ in the backward hidden sequence $\overleftarrow{m}_{T:1}$ are respectively:

$$\vec{m}_i = \text{GRU}(\vec{d}_i, \vec{m}_{i-1}),$$

$$\overleftarrow{m}_i = \text{GRU}(\vec{d}_i, \overleftarrow{m}_{i-1})$$

in which GRU(•) represents the activation function of the BGRU network. Based on the forward hidden sequence and the backward hidden sequence of the BGRU network, the intermediate representation vector h is:

$$h = \frac{1}{T}\sum_{i=1}^{T} m_i,$$

in which $m_i = [\vec{m}_i; \overleftarrow{m}_i]$ represents a concatenation between the $i^{st}$ element $\vec{m}_i$ in the forward hidden sequence $\vec{m}_{1:T}$ and the $i^{st}$ element $\overleftarrow{m}$ in the backward hidden sequence $\overleftarrow{m}_{T:1}$; and T represents the number of the dialogue features.

As shown in FIG. 5, a decoder 504 may be implemented by a forward gated recurrent unit (GRU) network and generates a series of dialogue feature vectors $\{\vec{d}'_1, \vec{d}'_2, \ldots, \vec{d}'_{T-1}, \vec{d}'_T\}$ by the input of the intermediate representation vector h outputted by the encoder 502. During the training of the encoder 502 and the decoder 504, the adopted objective function may be the mean square error (MSE) between the outputted dialogue feature vectors $\{\vec{d}'_1, \vec{d}'_2, \ldots, \vec{d}'_{T-1}, \vec{d}'_T\}$ and the inputted dialogue feature vectors $\{\vec{d}_1, \vec{d}_2, \ldots, \vec{d}_T\}$, with the computing formula as follows:

$$MSE = \frac{1}{N}\sum_{j=1}^{N}\sum_{i=1}^{T_j}\|\vec{d}'_i - \vec{d}_i\|^2,$$

in which N represents the number of the dialogue feature vectors in training data, and $\|\cdot\|^2$ represents L2 normal form. As the functions used by the encoder and the decoder are all derivable, the encoder and the decoder may be trained by adoption of the stochastic gradient decent (SGD) method.

As shown in FIG. 2A, the process of determining whether the triage task is successfully completed according to the intermediate representation in the step S206 includes: calculating the success probability of the completion of the triage task based on the previous intermediate representations and the intermediate representation, for instance, calculating the success probability of the completion of the triage task based on partial or all the previous intermediate representations and the current intermediate representation. The completion of the triage task may be the conclusion of the patient's illness, the determination of the affiliated department of the illness, and the recommendation of treatment recommendations, etc.

For instance, the process of determining whether the triage task is successfully completed according to the intermediate representation vector in the step S206' of FIG. 2B includes: calculating the success probability of the completion of the triage task based on the previous intermediate representation vectors and the intermediate representation vector, for instance, calculating the success probability of the completion of the triage task based on partial or all the previous intermediate representations and the current intermediate representation. For instance, in the step S206 of FIG. 2A and/or the step S206' of FIG. 2B, the process of determining whether the triage task is successfully completed may be characterized as Gaussian process, namely calculating the success probability p(y|h, H), in which: y∈ {−1, 1}; y=−1 represents triage failure; y=1 represents triage success; h represents the intermediate representation vector of the current dialogue; H represents the intermediate representation vector of the previous dialogue (for instance, the intermediate representation vectors of partial or all the previous dialogues are also referred to as the previous intermediate representation vectors).

p(y=1|h, H)=ϕ(ƒ(h|H)) may be defined, in which ϕ(•) represents the distribution function of standard normal distribution; ƒ(h|H) represents the potential function; and ƒ(h|H) maps the vector of the dim(h) dimension to a real number (namely $R^{dim(h)} \to R$). In the embodiment of the present invention, the potential function ƒ(•) is characterized as the Gaussian process, namely ƒ(h)~GP(m(h), k(h, h')), in which m(•) represents the mean value function, and k(.,.) represents the kernel function, with the computing formula as follows:

$$k(h, h') = p^2 \times \exp\left(-\frac{\|h - h'\|^2}{2l^2}\right) + \varepsilon_n^2,$$

in which exp(•) represents the exponential function based on the natural constant e, and $\varepsilon_n$ is used for noise modeling. The parameters p, l and $\varepsilon_n$ may perform parameter learning through the gradient-based method. Given the intermediate representation vector h of the current dialogue and the intermediate representation vector H of the previous dialogue, the posterior mean $\mu_*$ and the posterior variance $\sigma_*^2$ of ƒ(h) can be calculated (the computational method of the posterior mean $\mu_*$ and the posterior variance $\sigma_*^2$ may refer to Y Engel, S Mannor, and R Meir, 2005. Reinforcement learning with Gaussian processes. In Proceedings of ICML). The probability that the intermediate representation vector h of the current dialogue can successfully complete the triage task (namely the success probability) is:

$$p(y = 1 \mid h, H) = \phi\left(\frac{\mu_*}{\sqrt{1 + \sigma_*^2}}\right).$$

In the triage process, whether the current triage task is successfully completed must be determined. If the triage task has been completed, the device does not need to continue to interact with the user, so as to avoid the waste of the visiting time of the user. Of course, the user may feedback whether the triage task is successfully completed. For instance, every time the triage dialogue device answers a sentence, the user may select that the triage task has been completed or not completed. If the user selects that the triage task has been completed, the triage dialogue device ends this dialogue. However, this will increase the burden on the user and bring a bad experience to the user. Therefore, the embodiment of the present invention evaluates whether the current triage task requires user feedback or not through active learning method.

For instance, an uncertainty interval [λ, 1−λ] (0<λ<0.5), a failure interval [0, λ) and a success interval (λ, 1] may be set. When the success probability p falls into the failure interval [0, λ), the determination result of the step S206 and/or the step S206' is that the triage task is determined to have failed, which indicates that there is a high probability that the triage task has not been completed. At this point, the device needs to continue to interact with the user to ensure the completion of the task or adjust the dialogue policy. When the success probability p falls into the success interval (λ, 1], the determination result of the step S206 and/or the step S206' is that the triage task is determined to have been completed, which indicates that there is a high probability of completing the task. When the success probability p falls into the uncertainty interval [λ, 1−λ], the determination result of the step S206 and/or the step S206' is that whether the triage task is successfully completed is uncertain, and the dialogue policy must be adjusted (as shown by the step S208).

In the step S208, the process of adjusting the triage dialogue policy according to the determination result of the triage task includes:

S2080: continuing to interact with the user and/or adjusting the dialogue policy when the determination result is that the triage task is determined to have failed;

S2082: prompting the user to provide feedback information and determining whether to continue to interact with the user according to the feedback information, when the determination result is that whether the triage task is successfully completed is uncertain; or S2084: ending the dialogue with the user when the determination result is that the triage task is determined to have been completed.

For instance, in the step S2082, the process of determining whether to continue to interact with the user according to the feedback information when the determination result is that whether the triage task is successfully completed is uncertain includes: ending the dialogue with the user when the feedback information indicates that the triage task has been completed; or selecting information with the greatest information gain to interact with the user when the feedback information indicates that the triage task has not been completed.

For instance, the step of selecting the information with the greatest information gain to interact with the user in the process of adjusting the dialogue policy includes: calculating information gain of different symptoms, and determining symptoms relevant to the greatest information gain; and selecting the symptoms relevant to the greatest information gain to interact with the user.

Description will be given below to the operation of selecting the information with the greatest information gain to interact with the user by taking diseases and symptoms in Table 2 as an example. For clear and simple description of the examples, the description below is only limited to the diseases and the symptoms listed in the Table 2. However, the application of the device is not limited to 3 diseases and 8 symptoms in the Table 2. The device may be applied to any disease and any symptom. No limitation will be given here in the present invention.

TABLE 2

| Disease | Relation | Symptoms or Signs |
|---|---|---|
| Hypertension | Trigger | Headache, dizziness, nausea, polyuria |
| Migraine | Trigger | Headache, dizziness, nausea, vomit |
| Neurasthenia | Trigger | Headache, dizziness, insomnia, anxiety, irritability |

Supposing that a patient has symptoms of "headache" and "dizziness", at this point, the triage dialogue device is unable to determine that the patient suffers from which disease in the Table 2. The triage dialogue device needs to ask the patient more questions to gather information, so as to more accurately analyze the patient's condition. For instance, the triage dialogue device may ask "Do you have nausea symptom recently?", "Do you have polyuria symptom recently?", etc. More specifically, the device must determine a symptom at first and then ask the patient based on the symptom. For instance, the triage dialogue device may ask the patient "Do you have polyuria symptom recently?"; and if the patient answers yes, the triage dialogue device may conclude that the patient is very likely to have diabetes. Therefore, how to select a symptom to ask the patient is a problem to be solved. For instance, the triage dialogue device needs to select one symptom from the symptoms such as "nausea", "polyuria" and "vomit" to ask the patient. One illustrative solution is to select a symptom with the greatest information gain to ask the patient.

For instance, the computing formula of information gain is as follows:

IG(symptom)=$H$(diseases)−$H$(diseases|sympton), in which "symptom" represents the symptom; "diseases" represents the disease; and $H(\bullet)$ represents the entropy. For instance, IG(symptom) represents the information gain of the symptom; H(diseases) represents the entropy of diseases; and H(diseases|symptom) represents the entropy of diseases when the symptom is given.

Description will be given below to the computational process of information gain and the selection process of symptoms by taking two relevant symptoms nausea and polyuria of hypertension as an example. The device may respectively calculate the information gain of the two symptoms and select the symptom with the greatest information gain to ask the patient. Supposing that the probabilities that the patient has "hypertension", "migraine" and "neurasthenia" are all subject to uniform distribution, for instance, the probabilities are p(hypertension)=p(migraine)=p(neurasthenia)=⅓, in which p(•) represents the probability. In this case, the entropy of diseases is:

$$H(\text{diseases}) = -\frac{1}{3}\log_2^{\frac{1}{3}} - \frac{1}{3}\log_2^{\frac{1}{3}} - \frac{1}{3}\log_2^{\frac{1}{3}} = \log_2^3.$$

When the symptom is "nausea", the probabilities are p(hypertension)=½, p(migraine)=½, and p(neurasthenia)=0. The reason is that only the diseases hypertension and migraine have the nausea symptom in the example. At this point, as for the nausea symptom, if the entropy of diseases H(diseases|nausea) and the information gain of the nausea symptom IG(nausea) are:

$$H(\text{diseases}|\text{nausea}) = -\frac{1}{2}\log_2^{\frac{1}{2}} - \frac{1}{2}\log_2^{\frac{1}{2}} = \log_2^2,$$

$$IG(\text{nausea}) = H(\text{diseases}) - H(\text{diseases}|\text{nausea}) = \log_2^3 - \log_2^2 = \log_2^{1.5}.$$

When the symptom is "polyuria", the probabilities are p(hypertension)=1, p(migraine)=0, and p(neurasthenia)=0. The reason is that only the disease hypertension has the polyuria symptom in the example. At this point, as for the polyuria symptom, if the entropy of diseases H(diseases|polyuria) and the information gain of the polyuria symptom IG(polyuria) are:

$H$(diseases|polyuria)=−1×$\log_2^1$=0,

IG(polyuria)=$\log_2^3$−0=$\log_2^3$.

As the information gain of polyuria is greater than the information gain of nausea (namely IG(polyuria)>IG(nausea)), the device may select the "polyuria" symptom to ask the patient (for instance, asking a question "Do you have polyuria symptom recently?"). If the patient answers "yes", the disease is determined to be hypertension. If the answer is "no", hypertension is excluded, and the remaining diseases (as for the example, "migraine" and "neurasthenia") are taken as candidate diseases to repeat the above steps, until the disease is determined or the patient ends the process.

Figure 3:
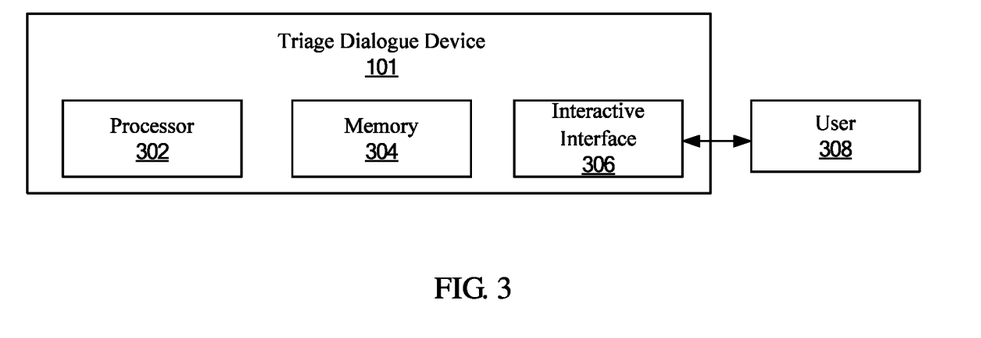
FIG. 3 is a schematic block diagram of a triage dialogue device provided by an embodiment of the present invention.

As shown in FIG. 3, the embodiment of the present invention further provides a triage dialogue device 101 based on active reward learning, which comprises: a processor 302 and a memory 304. The memory 304 is configured to store instructions, wherein the following operations are implemented when the instructions are executed by the processor 302: receiving triage dialogue content; dividing the triage dialogue content into a series of dialogue features, and generating dialogue feature vectors in one-to-one correspondence with the dialogue features; inputting the dialogue feature vectors into an encoder, and generating an intermediate representation vector through the encoder; determining whether the triage task is successfully completed according to the intermediate representation vector; and adjusting the triage dialogue policy according to the determination result of the triage task.

The processor 302 may process data signals and may include various kinds of computation structures such as a complex instruction set computer (CISC) architecture, a reduced instruction set computer (RISC) architecture, or a structure that implements multiple instruction set combinations. In some embodiments, the processor 302 may also be a microprocessor, e.g., an X86 processor or an ARM processor, or may also be a digital signal processor (DSP), etc. The processor 302 may control other components in the triage dialogue device 101 to execute expected functions.

The memory 304 may store instructions and/or data executed by the processor 302. For instance, the memory 304 may include one or more computer program products. The computer program products may include various kinds of computer-readable storage media, e.g., volatile memories and/or nonvolatile memories. The volatile memory, for instance, may include a random access memory (RAM) and/or a cache. The nonvolatile memory, for instance, may include a read only memory (ROM), a hard disk, a flash memory, etc. One or more computer program instructions may be stored on the computer-readable storage medium. The processor 302 may run the program instructions, so as to realize the triage dialogue function and/or other expected functions provided by the embodiment of the present invention. Various kinds of applications and various kinds of data, for instance, various kinds of data used and/or produced by the applications, may also be stored in the computer-readable storage medium.

For instance, the encoder adopts BGRU network; and based on the forward hidden sequence and the backward hidden sequence of the BGRU network, the intermediate representation vector h is:

$$h = \frac{1}{T}\sum_{i=1}^{T} m_i,$$

in which $m_i = [\vec{m}_i; \overleftarrow{m}_i]$ represents a concatenation between the $i^{st}$ element $\vec{m}_i$ in the forward hidden sequence $\vec{m}_{1:T}$ and the $i^{st}$ element $\overleftarrow{m}$ in the backward hidden sequence $\overleftarrow{m}_{T:1}$; and T represents the number of the dialogue features.

For instance, the operation of "determining whether the triage task is successfully completed according to the intermediate representation vector", implemented when the instructions are executed by the processor 302, includes: calculating the success probability of the completion of the triage task based on the previous intermediate representation vectors and the intermediate representation vector.

For instance, the process of determining whether the triage task is successfully completed is characterized as Gaussian process; and the success probability is:

$$p(y=1 \mid h, H) = \phi\left(\frac{\mu_*}{\sqrt{1+\sigma_*^2}}\right),$$

in which H represents partial or all the previous intermediate representation vectors; h represents the intermediate representation vector and is the current intermediate representation; $y \in \{-1, 1\}$, and $y=1$ represents the successful completion of the triage task; $\varphi(\cdot)$ represents the distribution function of standard normal distribution; $\mu_*$ and $\sigma_*^2$ respectively represent the posterior mean and the posterior variance of $f(h)$; and $f(\cdot)$ represents the potential function which is characterized as the Gaussian process.

For instance, when the success probability falls into a failure interval, the determination result is that the triage task is determined to have failed; when the success probability falls into an uncertainty interval, the determination result is that whether the triage task is successfully completed is uncertain; or when the success probability falls into a success interval, the determination result is that the triage task is determined to have been completed.

For instance, the operation of "adjusting the triage dialogue policy according to the determination result of the triage task", implemented when the instructions are executed by the processor 302, includes: continuing to interact with the user when the determination result is that the triage task is determined to have failed; prompting the user to provide feedback information and determining whether to continue to interact with the user according to the feedback information, when the determination result is that whether the triage task is successfully completed is uncertain; or ending the dialogue with the user when the determination result is that the triage task is determined to have been completed.

For instance, the operation of "determining whether to continue to interact with the user according to the feedback information when the determination result is that whether the triage task is successfully completed is uncertain", implemented when the instructions are executed by the processor 302, includes: ending the dialogue with the user when the feedback information indicates that the triage task has been completed; or selecting information with the greatest information gain to interact with the user when the feedback information indicates that the triage task has not been completed.

For instance, the operation of "selecting the information with the greatest information gain to interact with the user", implemented when the instructions are executed by the processor 302, includes: calculating information gain of different symptoms, and determining symptoms relevant to the greatest information gain; and selecting the symptoms relevant to the greatest information gain to interact with the user.

As shown in FIG. 3, the triage dialogue device 101 further comprises an interactive interface 306, wherein the interactive interface 306 is configured to interact with the user 308. The interactive interface 306 may include a microphone, a loudspeaker, a camera, buttons, a keyboard, a mouse, a display and/or a somatosensory device.

The embodiment of the present invention further provides a computer-readable storage medium. Computer instructions are stored on the computer-readable storage medium. The following operations are implemented when the computer instructions are executed by the processor: receiving triage dialogue content; dividing the triage dialogue content into a series of dialogue features, and generating dialogue feature vectors in one-to-one correspondence with the dialogue features; inputting the dialogue feature vectors into an encoder, and generating an intermediate representation vector through the encoder; determining whether the triage task is successfully completed according to the intermediate representation vector; and adjusting the triage dialogue policy according to the determination result of the triage task.

The computer-readable storage medium may include, for instance, a volatile memory and/or a nonvolatile memory. The volatile memory, for instance, may include an RAM and/or a cache. The nonvolatile memory, for instance, may include an ROM, a hard disk, a flash memory, etc. One or more computer program instructions may be stored on the computer-readable storage medium. The processor may run the program instructions, so as to realize the triage dialogue function provided by the embodiment of the present invention. Various kinds of applications and various kinds of data, for instance, various kinds of data used and/or produced by the applications, may also be stored in the computer-readable storage medium.

The description on the triage dialogue device 101 as shown in FIG. 3 and the computer-readable storage medium may refer to the description on the triage dialogue method 200 in FIG. 2A and the triage dialogue method 250 in FIG. 2B. No further description will be given here.

Figure 4:
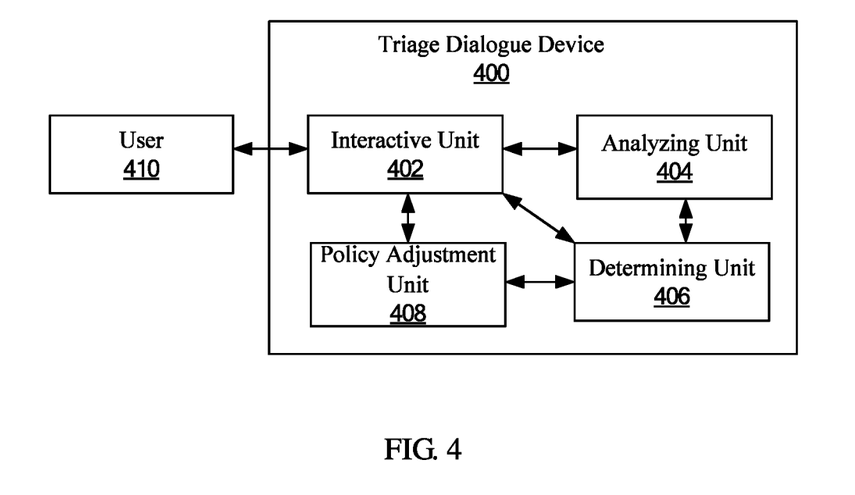
FIG. 4 is a schematic block diagram of a triage dialogue device provided by an embodiment of the present invention.

As shown in FIG. 4, the embodiment of the present invention further provides a triage dialogue device 400. The triage dialogue device 400 comprises an interactive unit 402, an analyzing unit 404, a determining unit 406 and a policy adjustment unit 408.

The triage dialogue device 400 may be implemented by software, hardware or a combination of software and hardware. In some embodiments, the interactive unit 402, the analyzing unit 404, the determining unit 406 and the policy adjustment unit 408 include codes and programs stored in the memory; and the processor may execute the codes and the programs to realize some or all the functions provided by the embodiment of the present invention.

In some embodiments, the interactive unit 402, the analyzing unit 404, the determining unit 406 and the policy adjustment unit 408 may be a special purpose hardware unit and are configured to realize some or all the functions provided by the embodiment of the present invention. For instance, the interactive unit 402, the analyzing unit 404, the determining unit 406 and the policy adjustment unit 408 may be a circuit board or a combination of a plurality of circuit boards. The circuit board or the combination of the plurality of circuit boards may include: (1) one or more processors; (2) one or more non-transitory computer-readable memories connected with the processors; and (3) firmware that can be executed by the processors and stored into the memories.

For instance, the interactive unit 402 is configured to receive triage dialogue content from a user 410. The interactive unit 402 may be the interactive interface 306 as shown in FIG. 3. The analyzing unit 404 is configured to generate intermediate representation of the triage dialogue content. The determining unit 406 is configured to determine whether the triage task is successfully completed according to the intermediate representation. The policy adjustment unit 408 is configured to adjust the triage dialogue policy according to the determination result of the triage task.

For instance, the intermediate representation is an intermediate representation vector. The analyzing unit 404 includes a decoder. The analyzing unit 404 is also configured to: divide the triage dialogue content into a series of dialogue features, and generate dialogue feature vectors in one-to-one correspondence with the dialogue features; and input the dialogue feature vectors into an encoder, and generate and output the intermediate representation vector through the encoder. The encoder adopts BGRU network.

The determining unit 406 is also configured to: calculate the success probability of the completion of the triage task based on the previous intermediate representations and the intermediate representation. For instance, the determining unit 406 is also configured to: calculate the success probability of the completion of the triage task based on the previous intermediate representation vectors and the intermediate representation vector. The determining unit 406 adopts the Gaussian process to determine whether the triage task is successfully completed. The success probability is:

$$p(y=1 \mid h, H) = \phi\left(\frac{\mu_*}{\sqrt{1+\sigma_*^2}}\right).$$

When the success probability falls into a failure interval, the determination result is that the triage task is determined to have failed; when the success probability falls into an uncertainty interval, the determination result is that whether the triage task is successfully completed is uncertain; or when the success probability falls into a success interval, the determination result is that the triage task is determined to have been completed.

The policy adjustment unit 408 is also configured to: continue to interact with the patient when the determination result is that the triage task is determined to have failed; prompt the patient to provide feedback information, and determine whether to continue to interact with the patient according to the feedback information, when the determination result is that whether the triage task is successfully completed is uncertain; or end the dialogue with the patient when the determination result is that the triage task is determined to have been completed.

When the determination result is that whether the triage task is successfully completed is uncertain, the policy adjustment unit 408 is also configured to: end the dialogue with the patient when the feedback information indicates that the triage task has been completed; or select information with the greatest information gain to interact with the patient when the feedback information indicates that the triage task has not been completed.

The policy adjustment unit 408 is also configured to: calculate information gain of different symptoms, and determine symptoms relevant to the greatest information gain; and select the symptoms relevant to the greatest information gain to interact with the patient.

In summary, the triage dialogue device, method and system, provided by the embodiment of the present invention, determine whether user feedback is needed by active learning method, reduce the burden on the user, and can rapidly and accurately complete the triage task.

In the text, relational terms such as first and second are used merely to distinguish one entity or operation from another entity or operation, and do not necessarily require or imply any such actual relationship or order between these entities or operations. Moreover, the term "comprise", "include" or any other variant thereof is intended to contain non-exclusive inclusions, so that a process, a method, an item, or a device that comprises a series of elements not only includes those elements but also includes other elements not explicitly listed, or also includes inherent elements of the process, the method, the item, or the device. In the case of no more limitation, an element defined by the sentence "comprising a . . . " does not exclude the existence of additional identical elements in the process, the method, the item or the device including the element.

Obviously, various changes and modifications may be made to the present invention by those skilled in the art without departing from the spirit and the scope of the present invention. In this case, if these changes and modifications of the present invention fall within the scope of the appended claims of the present invention and equivalents thereof, the present invention is also intended to include these changes and modifications.

The foregoing is only the preferred embodiments of the present invention and not intended to limit the scope of protection of the present invention. Any change or replacement that may be easily thought of by those skilled in the art within the technical scope disclosed by the present invention shall fall within the scope of protection of the present invention. Therefore, the scope of protection of the present invention shall be defined by the appended claims.

The invention claimed is:

1. A triage dialogue method, comprising:
receiving triage dialogue content;
dividing the triage dialogue content into a series of dialogue features, and generating dialogue feature vectors in one-to-one correspondence with the dialogue features;
inputting the dialogue feature vectors into an encoder, and generating an intermediate representation vector through the encoder;
determining whether a triage task is successfully completed according to the intermediate representation vector; and
adjusting a triage dialogue policy according to a determination result of the triage task,
wherein adjusting the triage dialogue policy according to the determination result of the triage task includes:
continuing to interact with a user when the determination result is that the triage task is determined to have failed;
prompting the user to provide feedback information and determining whether to continue to interact with the user according to the feedback information when the determination result is that whether the triage task is successfully completed is uncertain; or
ending the dialogue with the user when the determination result is that the triage task is determined to have been completed,
wherein prompting the user to provide feedback information and determining whether to continue to interact with the user according to the feedback information when the determination result is that whether the triage task is successfully completed is uncertain includes:
ending the dialogue with the user when the feedback information indicates that the triage task has been completed; or
selecting information with the greatest information gain to interact with the user when the feedback information indicates that the triage task has not been completed.

2. The triage dialogue method according to claim 1, wherein
the encoder adopts bidirectional gated recurrent unit (BGRU) network; and
based on a forward hidden sequence and a backward hidden sequence of the BGRU network, the intermediate representation vector h is:

$$h = \frac{1}{T}\sum_{i=1}^{T} m_i,$$

in which $m_i = [\vec{m}_i; \overleftarrow{m}_i]$ represents a concatenation between the $i^{st}$ element $\vec{m}_i$ in the forward hidden sequence $\vec{m}_{1:T}$ and the $i^{st}$ element $\overleftarrow{m}_i$ in the backward hidden sequence $\overleftarrow{m}_{T:1}$; and T represents the number of the dialogue features.

3. The triage dialogue method according to claim 1, wherein determining whether the triage task is successfully completed according to the intermediate representation vector includes:
calculating success probability of the completion of the triage task based on previous intermediate representation vectors and the intermediate representation vector.

4. The triage dialogue method according to claim 3, wherein
determining whether the triage task is successfully completed is characterized as Gaussian process; and the success probability is:

$$p(y = 1 | h, H) = \phi\left(\frac{\mu_*}{\sqrt{1+\sigma_*^2}}\right),$$

in which H represents the previous intermediate representation vectors; h represents the intermediate representation vector and is the current intermediate representation; $y \in \{-1, 1\}$, and $y=1$ represents the successful completion of the triage task; $\varphi(\bullet)$ represents the distribution function of standard normal distribution; $\mu_*$ and $\sigma_*^2$ respectively represent a posterior mean and a posterior variance of $f(h)$; and $f(\bullet)$ represents a potential function which is characterized as the Gaussian process.

5. The triage dialogue method according to claim 3, wherein
when the success probability falls into a failure interval, the determination result is that the triage task is determined to have failed;
when the success probability falls into an uncertainty interval, the determination result is that whether the triage task is successfully completed is uncertain; or
when the success probability falls into a success interval, the determination result is that the triage task is determined to have been completed.

6. The triage dialogue method according to claim 1, wherein selecting the information with the greatest information gain to interact with the user includes:
calculating information gains of different symptoms, and determining the symptom relevant to the greatest information gain; and
selecting the symptom relevant to the greatest information gain to interact with the user.

7. A triage dialogue device, comprising a processor and a memory, wherein the memory is configured to store instructions; and the following operations are implemented when the instructions are executed by the processor:
receiving triage dialogue content;
dividing the triage dialogue content into a series of dialogue features, and generating dialogue feature vectors in one-to-one correspondence with the dialogue features;
inputting the dialogue feature vectors into an encoder, and generating an intermediate representation vector through the encoder;
determining whether a triage task is successfully completed according to the intermediate representation vector; and
adjusting a triage dialogue policy according to a determination result of the triage task,
wherein adjusting the triage dialogue policy according to the determination result of the triage task includes:
continuing to interact with a user when the determination result is that the triage task is determined to have failed;
prompting the user to provide feedback information and determining whether to continue to interact with the user according to the feedback information when the determination result is that whether the triage task is successfully completed is uncertain; or ending the dialogue with the user when the determination result is that the triage task is determined to have been completed, wherein prompting the user to provide feedback information and determining whether to continue to interact with the user according to the feedback information when the determination result is that whether the triage task is successfully completed is uncertain includes:

ending the dialogue with the user when the feedback information indicates that the triage task has been completed; or selecting information with the greatest information gain to interact with the user when the feedback information indicates that the triage task has not been completed.

8. The triage dialogue device according to claim 7, wherein the encoder adopts BGRU network; and based on a forward hidden sequence and a backward hidden sequence of the BGRU network, the intermediate representation vector h is:

$$h = \frac{1}{T}\sum_{i=1}^{T} m_i,$$

in which $m_i = [\vec{m}_i; \overleftarrow{m}_i]$ represents a concatenation between the $i^{st}$ element $\vec{m}_i$ in the forward hidden sequence $\vec{m}_{1:T}$ and the $i^{st}$ element $\overleftarrow{m}_i$ in the backward hidden sequence $\overleftarrow{m}_{T:1}$; and T represents the number of the dialogue features.

9. The triage dialogue device according to claim 7, wherein determining whether the triage task is successfully completed according to the intermediate representation vector includes:

calculating success probability of the completion of the triage task based on the previous intermediate representation vectors and the intermediate representation vector.

10. The triage dialogue device according to claim 9, wherein determining whether the triage task is successfully completed is characterized as Gaussian process; and the success probability is:

$$p(y=1 \mid h, H) = \phi\left(\frac{\mu_*}{\sqrt{1+\sigma_*^2}}\right),$$

in which H represents the previous intermediate representation vectors; h represents the intermediate representation vector and is the current intermediate representation; $y \in \{-1, 1\}$, and $y=1$ represents the successful completion of the triage task; $\varphi(\cdot)$ represents the distribution function of standard normal distribution; $\mu_*$ and $\sigma_*^2$ respectively represent the posterior mean and the posterior variance of $f(h)$; and $f(\cdot)$ represents the potential function which is characterized as the Gaussian process.

11. The triage dialogue device according to claim 9, wherein when the success probability falls into a failure interval, the determination result is that the triage task is determined to have failed;

when the success probability falls into an uncertainty interval, the determination result is that whether the triage task is successfully completed is uncertain; or when the success probability falls into a success interval, the determination result is that the triage task is determined to have been completed.

12. The triage dialogue device according to claim 7, wherein selecting the information with the greatest information gain to interact with the user includes:

calculating information gains of different symptoms, and determining the symptom relevant to the greatest information gain; and selecting the symptom relevant to the greatest information gain to interact with the user.

13. The triage dialogue device according to claim 7, further comprising an interactive interface, wherein the interactive interface is configured to interact with the user.

14. A non-transitory computer-readable storage medium, wherein computer instructions are stored on the computer readable storage medium; and the following operations are implemented when the computer instructions are executed by a processor:

receiving triage dialogue content;

dividing the triage dialogue content into a series of dialogue features, and generating dialogue feature vectors in one-to-one correspondence with the dialogue features;

inputting the dialogue feature vectors into an encoder, and generating an intermediate representation vector through the encoder;

determining whether a triage task is successfully completed according to the intermediate representation vector; and adjusting a triage dialogue policy according to a determination result of the triage task, wherein adjusting the triage dialogue policy according to the determination result of the triage task includes:

continuing to interact with a user when the determination result is that the triage task is determined to have failed;

prompting the user to provide feedback information and determining whether to continue to interact with the user according to the feedback information when the determination result is that whether the triage task is successfully completed is uncertain; or ending the dialogue with the user when the determination result is that the triage task is determined to have been completed, wherein prompting the user to provide feedback information and determining whether to continue to interact with the user according to the feedback information when the determination result is that whether the triage task is successfully completed is uncertain includes:

ending the dialogue with the user when the feedback information indicates that the triage task has been completed; or selecting information with the greatest information gain to interact with the user when the feedback information indicates that the triage task has not been completed.

* * * * *